United States Patent [19]

Sugimoto

[11] Patent Number: 4,621,052

[45] Date of Patent: Nov. 4, 1986

[54] PROCESS FOR THE PRODUCTION OF HUMAN EPIDERMAL GROWTH FACTOR

[75] Inventor: Kaname Sugimoto, Okayama, Japan

[73] Assignee: Kabushiki Kaisha Hayashibara Seibutsu Kagaku Kenkyujo, Okayama, Japan

[21] Appl. No.: 619,708

[22] Filed: Jun. 14, 1984

Related U.S. Application Data

[63] Continuation-in-part of Ser. No. 322,185, Nov. 17, 1981, abandoned.

[30] Foreign Application Priority Data

Dec. 11, 1980 [JP] Japan .................................. 55-174854

[51] Int. Cl.$^4$ ...................... C12P 21/00; C12N 15/00; C12N 5/00; C12N 5/02
[52] U.S. Cl. .................................. 435/68; 435/172.2; 435/240; 435/241; 435/284; 435/948; 530/399; 935/106; 935/109
[58] Field of Search ................ 435/1, 6, 172.2, 172.3, 435/240, 241, 68, 948, 248, 284, 286; 436/548; 424/85-87; 260/112 B, 112 R; 935/106, 109; 530/399

[56] References Cited

U.S. PATENT DOCUMENTS

| | | | |
|---|---|---|---|
| 3,917,824 | 11/1975 | Camble et al. | 424/177 |
| 4,135,975 | 1/1979 | Lichtman et al. | 195/1.8 |
| 4,242,460 | 12/1980 | Chick et al. | 435/283 |
| 4,276,282 | 6/1981 | Sugimoto et al. | 425/85 |
| 4,285,929 | 8/1981 | Sugimoto | 424/85 |
| 4,328,207 | 5/1982 | Sugimoto | 424/85 |
| 4,377,513 | 5/1983 | Sugimoto et al. | 260/112 R |
| 4,383,034 | 5/1983 | Sugimoto | 435/70 |
| 4,383,035 | 5/1983 | Sugimoto | 435/70 |
| 4,383,036 | 5/1983 | Sugimoto | 435/70 |

OTHER PUBLICATIONS

Zeleznik et al., *Endocrinology*, 1979, vol. 105, pp. 156-162.

Lewin, *Gene Expression*, 2nd ed., John Wiley and Sons, N.Y., 1980, pp. 258-265.

Pattill, Hormone Synthesis and Function in vitro, *Growth, Nutrition and Metabolism of Cells in Culture*, Academic Press, N.Y., 1972, p. 243.

Bordelon et al, Human Glycoprotein Hormone Production in Human-Human and Human-Mouse Somatic Cell Hybrids, *Chem. Abst.*, vol. 86, 1977, p. 246.

Astaldi et al, *J. of Immunology*, vol. 125, No. 4, 1411-1414, Oct. 1980.

Peterson, J. A. et al, "Expression of Differentiated Functions in Hepatoma Cell Hybrids: Induction of Mouse Albumin Production in Rat Hepatoma-Mouse Fibroblast Hybrids", *Proc. Nat. Acad. Sci.*, 69:3, 571-75 (1972).

Malawista, S. E. et al, 37 Expression of Differentiated Functions in Hepatoma Cell Hybrids: High Frequency of Induction of Mouse Albumin Production in Rat Hepatoma-Mouse Lymphoblast Hybrids": *Proc. Nat. Acad. Sci.*, 71:3, 927-31 (1974).

Elder, J. B.: Cellular Localisation of Human Urogastrone/Epidermal Growth Factor: *Nature*, vol. 271, 466-467 (1978).

Carpenter, Graham, "The Regulation of Cell Proliferation: Advances in the Biology and Mechanism of Action of Epidermal Growth Factor", *The Journal of Investigative Dermatology*, 71, 283-87 (1978).

Hollenberg, M. D., "Epidermal Growth Factor-Urogastrone, a Polypeptide Acquiring Hormonal Status", *Vitamins and Hormones*, vol. 37, pp. 69-110 (1979).

Friedman, M. H. F., "Urinary Gastric Secretory Depressants (Urogastrone)", *Vitamins and Hormones*, vol. 9, 313-353 (1951).

Hirata, Y. et al, "Epidermal Growth Factor (Urogastrone) in Human Tissues", *Journal of Clinical Endocrinology and Metabolism*, 48:4, pp. 667-672 (1979).

Thompson, J. S. et al, "Heterologous Transplantation of Mouse Tumors into the Newborn Albino Rat", *Cancer Research*, vol. 20, pp. 1365-1371 (1960).

Bordelon, M. R. et al, "Human Glycoprotein Hormone Production in Human-Human and Human-Mouse Somatic Cell Hybrids", *Exp. Cell Research*, 103 (1976) 303-310.

*Primary Examiner*—Sidney Marantz
*Assistant Examiner*—Patricia L. DeSantis
*Attorney, Agent, or Firm*—Browdy and Neimark

[57] ABSTRACT

The present invention relates to a process for the production of human epidermal growth factor (hEGF). More precisely, the present invention relates to a process for the mass production of hEGF, comprising in vivo or in vitro multiplication of human cells capable of producing hEGF, and in vitro cultivation of the multiplied human cells to produce hEGF. The hEGF production according to the present invention is much higher than that attained by conventional processes; thus, hEGF can be obtained in a sufficient amount for use in the prevention and treatment of human diseases.

21 Claims, No Drawings

PROCESS FOR THE PRODUCTION OF HUMAN EPIDERMAL GROWTH FACTOR

This application is a continuation-in-part, of application Ser. No. 322,185, filed 11-17-81, abandoned.

DETAILED DESCRIPTION OF THE INVENTION

The present invention relates to a process for the production of human epidermal growth factor (urogastrone, abbreviated as hEGF hereinafter).

As described in M. H. F. Friedman, *Vitamins and Hormones*, Vol. 9, pp. 313-353 (1951), hEGF is a biologically-active substance, originally found in human urine and having been classified into a family of "gastrone substances" which suppress the secretion of gastric juices from the digestive system. Since the finding of its strong anti-ulcer and growth-stimulating actions in various tissues in addition to the above described property, the mass production of hEGF sufficient for medical applications has been in great expectation. Although conventional processes such as those by recovery from human urine via very complicated steps are known, they cannot provide a sufficient amount of homogenous hEGF with a well-defined quality for practical clinical trials.

The present inventor has investigated processes for the mass production of hEGF which is so homogenous and high-titered as to enable its utilization in clinical trials. These efforts have resulted in the unexpected finding that a large amount of hEGF can be obtained by multiplication of certain human cells capable of producing hEGF, using in vitro tissue culture or in vivo culture in a non-human warm-blooded animal, followed by in vitro cultivation of the multiplied human cells to produce said substance. Particularly, the invention relates to a process for the production of hEGF, characterized in multiplying human cells capable of producing hEGF either by culturing the cells in a nutrient medium, by transplanting the cells to a non-human warm-blooded animal body, or by allowing the cells to multiply with a device by which the nutrient body fluid of a non-human warm-blooded animal is supplied to the cells; and then allowing the human cells multiplied by any of the above multiplication procedures to release hEGF.

As to the human cells usable in the present invention, any human cells can be used so far as they produce hEGF and are transplantable to an in vitro nutrient medium or a non-human warm-blooded animal body and multipliable therein. Preferable human cells are submaxillary gland cells, thyroid cells, spleen cells, kidney cells, duodenal cells and jejunal cells; those transformed with carcinogenic virus or agent, or radiation; tumor cells from a patient suffering from submaxillary gland tumor, lung carcinoma or bladder carcinoma; and established cell lines of the above cells.

The use of easily maintainable human lymphoblastoid lines into which have been introduced the hEGF production governing genetic sites of the above described cells by means of genetic recombination technique using enzymes such as DNA ligase, nuclease and DNA polymerase, or by cell fusion using agents such as polyethylene glycol or Sendai virus, conveniently results in an about 2-10-fold higher or more hEGF production per cell as well as in a much higher cell multiplication efficiency. Furthermore, since the use of such human lymphoblastoid lines results in the formation of easily disaggregatable massive tumors when the lines are transplanted to the animal body, the multiplied live human lymphoblastoid cells can be harvested easily.

Such human lymphoblastoid lines are obtained by establishing human lymphoblastoid cells from a patient suffering from a leukemia, e.g. acute lymphatic leukemia, chronic myelogenous leukemia, malignant lymphoma, Burkitt lymphoma, or acute myelogenous anemia, or infectious mononucleosis, in a suitable manner. Usable human lymphoblastoid lines may be obtained by transforming normal human lymphocytes by use of a suitable carcinogenic virus, agent or irradiation, such as Epstein-Barr virus (EB virus), mitogen or x-ray irradiation, and establishing the obtained lymphoblastoid cells, for example, B-Ta, Q-Ta, B-Ue, Q-Ue, B-Ke, and Q-Ku, reported in *Protein, Nucleic Acid and Enzyme*, vol. 20, No. 6, pp. 616-643 (1975). Preferably, the human lymphoblastoid line is of leukemic origin as, for example, Namalwa, reported by Strander, H. et al, *Journal of Microbiology*, Vol. 1, pp. 116-117 (1975), BALL-1, TALL-1 and NALL-1, reported by Miyoshi, I. et al, *Nature*, vol. 267, No. 4614, pp. 843-844 (1977), or JBL reported by Miyoshi, I. et al, *Cancer*, vol. 40, pp. 2999—3003 (1977). Other lymphoblastoid cell lines usable include the other human lymphoblastoid cell lines listed in the above cited Strander et al publication, including Akuba, P3HR-1 and LY-46. Others include the cell lines of N-7002 and B-7101 as described in *Journal of Immunology*, vol. 113, pp. 1334-1345 (1974); EBV-Sa, EBV-Wa, MOLT-3 and EBV-HO, as described in *The Tissue Culture*, vol. 6, No. 3, pp. 527-546 (1980); CCRF-SB (ATCC CCL 120); BALM 2; DND-41; etc.

As to the methods for cell multiplication employable in the present invention, two methods can be employed: one is the in vitro tissue culture method in which the human cells capable of producing hEGF are inoculated in a nutrient medium and multiplied therein; and another is the in vivo method in which the human cells are transplanted to a non-human warm-blooded animal body or suspended in a device by which the nutrient body fluid of a non-human warm-blooded animal is supplied to the cells, and multiplied therein or therewith.

First, the in vitro multiplication procedure is explained by the following description.

As to the nutrient media usable in the procedure, any nutrient media can be used so far as the human cells multiply therein. Preferable nutrient media are those which contain usually L-arginine, L-histidine, L-lysine, L-tyrosine, L-tryptophan, L-methionine, L-serine, L-glycine and cysteine as nitrogen sources, carbohydrates such as glucose, inositol, ribose and deoxyribose, and minerals essential for the cell growth such as $Na^+$, $K^+$, $Cl^-$, $Fe^{++}$, $Fe^{+++}$, $Co^{++}$, $Ca^{++}$, $PO_4^{--}$ and others. The nutrient media can be supplemented, if necessary, with other growth factors such as hormones and/or vitamins. Also, various conventional nutrient media can be employed in the procedure. One of such conventional nutrient media is RPMI 1640 medium which may be supplemented further with vitamins, minerals, carbohydrates, amino acids and about 0.5-20 v/v % mammalian serum prior to use.

As to the in vitro cultivation for the cell multiplication, any method can be employed in this procedure so far as the inoculated human cells multiply thereby. The tissue culture vessel usable in this procedure is usually a jar fermenter, bottle, flask or stainless-steel tank, and equipped, if necessary, with a shaker and/or rotary agitator. In the case of mono-layer culture, the cultivation can be carried out with inert and water-insoluble supports such as glass beads, glass rods or metal beads including those with titanium, synthetic polymer, dextran gel or ceramics which provides the growing human cell with a wider area to allow the cell to form colonies. In the case of suspension culture, the cultivation should be carried out and continued to obtain a maxium cell density under aerobic and agitation conditions.

As to the conditions for the cell inoculation and multiplication, any conditions can be applied so far as the human cells multiply thereby; for example, the cultivation temperature may be about 20°–40° C., preferably, about 35°–38° C., and inoculum, expressed by the number of cells per ml medium with which maximum cell growth can be obtained within about one week after the cell inoculation, is preferably about $10^4$–$10^6$ cells per ml medium.

The human cells implanted in the nutrient medium should be multiplied by incubating within the above temperature range for about 5-9 days while replacing periodically the medium with a fresh one to supply sufficient nutrients to the cells and to dilute and remove the cells metabolites in the medium. Since during the cell multiplication a small amount of hEGF may be released in the medium, it can be harvested from the medium upon the replacement of medium.

The following description illustrates the in vivo multiplication procedure.

According to the in vivo multiplication procedure, the human cells capable of producing hEGF can be multiplied easily while utilizing the nutrient body fluid supplied from a non-human warm-blooded animal body by transplanting the cells to the animal body, or suspending the cells in a conventional diffusion chamber devised to receive the nutrient body fluid, and feeding the animal in the usual way. Accordingly, a large amount of hEGF can be obtained easily with no, or much less, nutrient medium containing expensive serum for the cell multiplication than in the case of in vitro tissue culture. Also, the procedure is characterized by stabler and higher cell multiplication, and higher hEGF production per cell as well as by easier maintenance of the culture medium during cell multiplication.

As to the non-human warm-blooded animals usable in the procedure, any non-human warm-blooded animal can be used so far as the human cells multiply therein. For example, poultry, such as chicken and pigeon, or a mammalian, such as dog, cat, monkey, goat, pig, cow, horse, guinea pig, rat, hamster, mouse and nude mouse, is advantageously feasible in the present invention. Since transplantation of the human cells to the animal may elicits undesirable immunoreaction, the use of a newborn or infant animal, or those in the youngest possible stage, for example, egg, embryo or foetus, is desirable. In order to reduce the immunoreaction as much as possible, prior to the cell transplantation, the animal may be treated wit X-ray or γ-ray irradiation, about 200–600 rem, or injection of antiserum or immunosuppressive agent prepared according to conventional methods. Since nude mouse, used as the host animal, exhibits less immunoreaction even when in its adulthood, any of the human cell lines can be transplanted therein without such pretreatment, and multiplied rapidly.

Both stabilized cell multiplication and enhancement of hEGF production can be carried out by repeated transplantation using combination(s) of different non-human warm-blooded animals; these objectives are attainable, for example, by first the implanting the cells in hamsters and multiplying therein, and then reimplanting in nude mice. The repeated transplantation may be carried out with animals of the same class or division as well as those of the same species or genus.

As to where the human cells are implantable, the human cells can be implanted in any site of the animal so far as they multiply therein; for example, in the allantoic cavity, or intravenously, intraperitoneally, or subcutaneously.

In addition to the above described direct cell transplantation, any of the conventional human cell lines capable of producing hEGF can be multiplied easily while utilizing the nutrient body fluid supplied from the animal body by embedding, for example, intraperitoneally, in said animal body a conventional diffusion chamber, of any of various shapes and sizes, equipped with a porous membrane filter, ultra filter or hollow fiber having a pore size of about $10^{-7}$–$10^{-5}$ m in diameter which prevents contamination of the chamber with the host animal cells and allows the animal to supply the cells with its nutrient body fluid. Additionally, the diffusion chamber can be designed, if necessary, so it could be placed, for example, on the hose animal, and the body fluid from the animal body allowed to circulate into the chamber, to enable observation of the cell suspension in the chamber through transparent side window(s), equipped on the chamber wall(s), and to enable replacement and exchange with a fresh chambers. Cell production per host thereby increases to a further higher level over the period of the animal life without sacrifice of the host animal. Furthermore, when the diffusion chamber is used, since slight immunoreaction is elicited due to the absence of the direct contact of the human cells with the host animal cells, various non-human warm-blooded animals can be used as the host without such pretreatment to reduce their immunoreaction.

Feeding of the host animal can be carried out by conventional methods even after the cell transplantation, and no special care is required.

Maximum cell multiplication can usually be attained within 1–20 weeks after the cell transplantation. When the human cell line transplanted to the animal body is a human tumor cell line or human lymphoblastoid line, the maximum cell multiplication can be attained within 1–5 weeks after the cell transplantation due to their much higher cell multiplication efficiencies.

According to the procedure, the number of human cells obtained per host is about $10^7$–$10^{12}$ or more. In other words, the number of human cells transplanted to the animal increases about $10^2$–$10^7$-fold or higher, or about $10^1$–$10^6$-fold or higher than that attained by in vitro cultivation using a nutrient medium; thus, the multiplied human cells can be advantageously usable in the mass production of hEGF.

As to the methods by which the human cells multiplied by any of the above described multiplication procedures are allowed to release hEGF, any method can be employed so far as the multiplied human cells release said substance thereby. For example, the human cells, obtained by in vitro mono-layer culture or suspension culture, by multiplying in ascite in suspension and harvesting from said ascite, or by extracting the massive tumor formed subcutaneously and harvesting after the disaggregation of the massive tumor, are suspended to give a cell concentration of about $10^4$–$10^8$ cells per ml in a nutrient medium, prewarmed at a temperature of about 20°–40° C., and then incuabted at this temperature for several hours or days to produce hEGF.

The hEGF thus obtained can be collected easily by purification and separation techniques using conventional procedures such as salting-out, dialysis, filtration, centrifugation, concentration and lyophilization. If a further purified hEGF preparation is desirable, a preparation of the highest purity can be obtained by the above mentioned techniques in combination with one or more other procedures, such as adsorption and desorption with ion exchange, fractionation by molecular weight, affinity chromatography, isoelectric point fractionation and electrophoresis.

The hEGF preparation thus obtained is immunologically identical with those from human urine by conventional processes, and not contaminated with hepatitis virus or pyrogens. Therefore, the preparation can be advantageously used alone or in combination with one or more agents for injection, external, internal or diagnostical administration in the prevention and treatment of various human diseases.

Throughout the present SPECIFICATION, the hEGF production as determined by the radio-receptor assay method as described in Roger L. Ladda et al., Analytical Chemistry, Vol. 93, pp. 286-294 (1979), and expressed by weight.

The following description illustrates the embodiments of the present invention; they are not to be construed as limiting the scope of the invention.

EXAMPLE 1

Disaggregated human submaxillary gland tumor cells, obtained by extracting from a patient suffering from submaxillary gland tumor and mincing, were inoculated to give a cell concentration of about $1 \times 10^5$ cells per ml in Earle's 199 medium (pH 7.4), supplemented with 10 v/v % foetal calf serum. Thereafter, the resultant was incubated in a closed vessel at 37° C. for one week while replacing periodically the medium with a fresh one. After reaching confluency, the mono-layer was washed with a physiological saline solution containing trypsin and phosphate.

The trypsinized cells were resuspended to give a cell concentration of about $1 \times 10^5$ cells per ml in a fresh preparation of the same medium, and the resulting cell suspension was incubated at 37° C. and pH 7.4 for one week. Thereafter, the cells were ultra-sonicated, and the hEGF in the resulting supernatant was determined. The hEGF production was about 1.3 $\mu$g per ml cell suspension.

EXAMPLE 2

The human submaxillary gland tumor cells obtained as in Example I and a human Namalwa leukemic lymphoblastoid line were suspended together in a vessel with a salt solution, containing 140 mM NaCL, 54 mM KCl, 1 mM NaH$_2$PO$_4$ and 2 mM CaCl$_2$, to give a respective cell concentration of about $1 \times 10^4$ cells per ml. The cell suspension was mixed under ice-chilling conditions with a fresh preparation of the same salt solution containing UV-irradiation preinactivated Sendai virus, transferred into a 37° C. incubator five minutes after the mixing, and stirred therein for 30 minutes to effect cell fusion, introducing the hEGF producibility of the human submaxillary gland tumor cells into the human leukemic lymphoblastoid line.

After cloning, according to conventional methods, a hybridoma cell strain capable of producing hEGF, the hybridoma cell strain was multiplied similarly as in EXAMPLE 1, and the multiplied hybridoma cells were treated similarly as in the same EXAMPLE to produce hEGF. The hEGF production was about 5.8 $\mu$g per ml cell suspension.

EXAMPLE 3

Adult nude mice were implanted subcutaneously with human submaxillary gland tumor cells, obtained similarly as in EXAMPLE 1, and then fed in the usual way for four weeks. The resulting massive tumor formed subcutaneously, about 10 g each, and were extracted and disaggregated by mincing and suspending in a physiological saline solution containing trypsin.

After washing the trypsinized cells with Earle's 199 medium (pH 7.4), supplemented with 10 v/v % foetal calf serum, the cells were resuspended to give a cell concentration of about $1 \times 10^5$ cells per ml in a fresh preparation of the same medium, and then incubated at 37° C. for seven days to produce hEGF. Thereafter, the cells were ultra-sonicated, and the hEGF in the resulting supernatant was determined. The hEGF production was about 23 $\mu$g per ml cell suspension.

EXAMPLE 4

Adult nude mice were implanted intraperitoneally with a human Namalwa leukemic lymphoblastoid line in which the hEGF producibility of the human submaxillary gland tumor cells was introduced similarly as in EXAMPLE 2, and then fed in the usual way for five weeks. The resulting massive tumors, about 15 g each, were treated similarly as in EXAMPLE 3 to produce hEGF. The hEGF production was about 320 $\mu$g per ml cell suspension.

EXAMPLE 5

After injection of antiserum, prepared from rabbits according to the conventional method, into newborn hamsters to reduce their immunoreaction, the animals were implanted subcutaneously with a human Namalwa leukemic lymphoblastoid line in which the hEGF producibility of a human lung carcinoma line A-549 was introduced similarly as in EXAMPLE 2, and then fed in the usual way for three weeks. The resulting massive tumors formed subcutaneously, and about 10 g each, and were extracted and treated similarly as in EXAMPLE 3 to produce hEGF. The hEGF production was about 250 $\mu$g per ml cell suspension.

EXAMPLE 5-A (Control)

In order to compare the hEGF productivity of the lymphoblastoid hybridoma cell, according to one aspect of the present invention, with the hEGF productivity of a fibroblastoid hybridoma cell using the same hEGF producing human cell, the following control experiment was conducted. The human submaxillary gland tumor cells were fused with a human lung fibroblastoid cell line, WI-26, ATCC CCL 95, similarly as in Example 2. The obtained hybridoma cells capable of producing hEGF were cultured in vivo as in Example 3 to produce hEGF. The hEGF production was only about 0.1 $\mu$g per ml of the cell suspension.

Separately, the hybridoma cells were implanted intraperitoneally into adult nude mice, which were then fed in the usual way for five weeks. The resultant massive tumors, about 2 g each, were extracted, disaggregated, and cultured in vitro similarly as in Example 3 to produce hEGF. The hEGF production so obtained was approximately 0.1 μg per ml of cell suspension.

EXAMPLE 6

Newborn rats were implanted intravenously with a human BALL-I leukemic lymphoblastoid line in which the hEGF producibility of human bladder carcinoma cells, obtained from a patient suffering from bladder carcinoma, was introduced similarly as in the EXAMPLE 2, and then fed in usual way for four weeks. The resulting massive tumors, about 30 g each, were extracted and treated similarly as in EXAMPLE 3 to produce hEGF except that Earle's 199 medium was replaced with RPMI 1640 medium. The hEGF production was about 170 μg per ml cell suspension.

EXAMPLE 7

After about 400 rem X-ray irradiation of adult mice to reduce their immunoreaction, the animals were implanted subcutaneously with human submaxillary gland tumor cells, obtained similarly as in the EXAMPLE 1, and then fed in usual way for four weeks. The resulting massive tumors formed subcutaneously and about 15 g each, and were extracted and treated similarly as in EXAMPLE 3 to produce hEGF. The hEGF production was about 35 μg per ml cell suspension.

EXAMPLE 8

A human BALL-I leukemic lymphoblastoid line in which the hEGF producibility of human bladder carcinoma cells was introduced similary as in EXAMPLE 6 was suspended in physiological saline solution, and the resulting cell suspension was transferred into a plastic cylindrical diffusion chamber, inner volume about 10 ml, equipped with a membrane filter having a pore size of about 0.5μin diameter. After intraperitoneal embedding of the chamber into an adult rat, the animal was fed in the usual way for four weeks, and the chamber was removed. The human cell density in the chamber attained by the above operation was about $2 \times 10^9$ cells per ml which was about $10^3$-fold higher or more than that attained by in vitro cultivation using a $CO_2$ incubator.

The multiplied human cells were treated similarly as in EXAMPLE 6 to produce hEGF. The hEGF production was about 220 μg per ml cell suspension.

EXAMPLE 9

A human JBL leukemic lymphoblastoid line in which the hEGF producibility of the human lung carcinoma line A-549 was introduced similarly as in EXAMPLE 5 was implanted in allantoic cavities of embryonated eggs which had been preincubated at 37° C. for five days. After further incubation of the eggs at this temperature for an additional one week, the multiplied human cells were harvested.

The human cells thus obtained were treated similarly as in EXAMPLE 1 to produce hEGF. The hEGF production was about 130 μg per ml cell suspension.

EXAMPLE 10

A normal human lymphoblastoid cell line, EBV-Wa, obtained by transforming normal human lymphocytes with EB virus, was fused with human submaxillary gland tumor cells similarly as in Example 2. The obtained hybridoma cells capable of producing hEGF were implanted intraperitoneally into adult nude mice, and the animals were fed in the usual way for five weeks. The resultant massive tumors, about 9 g each, were disaggregated by extracting, mincing and suspending in a physiological saline solution containing trypsin. The multiplied cells so obtained were cultured in vitro similarly as in Example 3 to produce hEGF. The hEGF level was about 110 μg per ml of the cells suspension.

What we claim is:

1. A process for producing human epidermal growth factor (hEGF), comprising:
   culturing human tumor forming cells capable of producing hEGF on a culture medium under conditions appropriate to accumulate a substantial amount of hEGF; and
   recovering the accumulated hEGF from the culture.

2. A process in accordance with claim 1, wherein said human cells capable of producing hEGF are human submaxillary gland tumor cells.

3. A process in accordance with claim 1, wherein said human cells capable of producing hEGF are human lung carcinoma cells.

4. A process in accordance with claim 1, wherein said human cells capable of producing hEGF are human bladder carcinoma cells.

5. A process for producing human epidermal growth factor (hEGF) comprising:
   culturing hybridoma cells of hEGF-producing human cells and a human lymphoblastoid line on a culture medium under conditions appropriate to accumulate a substantial amount of hEGF; and
   recovering the accumulated hEGF from the culture.

6. A process in accordance with claim 5, wherein said hEGF-producing human cells are human submaxillary gland tumor cells.

7. A process in accordance with claim 5, wherein said hEGF-producing human cells are human lung carcinoma cells.

8. A process in accordance with claim 5, wherein said hEGF-producing human cells are human bladder carcinoma cells.

9. A process in accordance with claim 5, wherein said human lymphoblastoid line is of leukemic origin.

10. A process in accordance with claim 5, wherein said human lymphoblastoid line is a member selected from the group consisting of Namalwa, JBL, and BALL-1.

11. A process in accordance with claim 5, wherein said hybridoma cells are obtained by:
    suspending hEGF-producing human cells together with a human lymphoblastoid line in a salt solution containing an effective amount of a cell fusion inducing agent;
    allowing the resultant cell suspension to stand for a period sufficient to effect cell fusion; and
    selecting or cloning hybridoma cells capable of producing hEGF.

12. A process in accordance with claim 11, wherein said cell fusion inducing agent is an activated Sendai virus or polyethylene glycol.

13. A process in accordance with claim 5, wherein said hybridoma cells used in said culturing step are multiplied hybridoma cells obtained by:
    implanting said hybridoma cells in an immunodeficient or immunosuppressed non-human warm-blooded animal;

feeding the animal to allow said hybridoma cells to utilize the nutrient body fluid of the animal for their multiplication; and extracting and disaggregating the resultant tumor, formed in the animal, to obtain the multiplied hybridoma cells.

14. A process in accordance with claim 13, wherein said hybridoma cells used in said implanting step are obtained by:

suspending hEGF-producing human cells together with a human lymphoblastoid line in a salt solution containing an effective amount of a cell fusion inducing agent;

allowing the resultant cell suspension to stand for a period sufficient to effect cell fusion; and selecting or cloning hybridoma cells capable of producing hEGF.

15. A process in accordance with claim 13, wherein said non-human warm-blooded animal is a fowl or a mammalian.

16. A process in accordance with claim 13, wherein said non-human warm-blooded animal is a member selected from the group consisting of chicken, pigeon, dog, cat, monkey, goat, pig, cow, horse, guinea pig, rabbit, rat, hamster, nude mouse and mouse.

17. A process in accordance with claim 5, wherein said hybridoma cells used in said culturing step are multiplied hybridoma cells obtained by:

suspending said hybridoma cells in a device in which the nutrient body fluid of a non-human warm-blooded animal can be supplied to said hybridoma cells;

embedding or placing said device in or on a non-human warm-blooded animal in a manner such that the nutrient body fluid of said animal is supplied to the hybridoma cells within said device;

feeding said animal to allow said hybridoma cells to utilize the nutrient body fluid for their multiplication; and harvesting the multiplied hybridoma cells from the device.

18. A process in accordance with claim 17, wherein said hybridoma cells used in said suspending step are obtained by:

suspending hEGF-producing human cells together with a human lymphoblastoid line in a salt solution containing an effective amount of a cell fusion inducing agent;

allowing the resultant cells suspension to stand for a period sufficient to effect cell fusion; and selecting or cloning hybridoma cells capable of producing hEGF.

19. A process in accordance with claim 17, wherein said device is a diffusion chamber equipped with a membrane filter, ultra filter or hollow fiber having a nominal pore size in the range of $10^{-7}$ to $10^{-5}$ m.

20. A process in accordance with claim 17, wherein said non-human warm-blooded animal is a fowl or a mammalian.

21. A process in accordance with claim 17, wherein said non-human warm-blooded animal is a member selected from the group consisting of chicken, pigeon, dog, cat, monkey, goat, pig, cow, horse, guinea pig, rabbit, rat, hamster, nude mouse and mouse.

* * * * *